(12) United States Patent
Landry

(10) Patent No.: US 7,789,827 B2
(45) Date of Patent: Sep. 7, 2010

(54) VARIABLE SHAFT FLEXIBILITY IN ENDOSCOPE

(75) Inventor: Dana J. Landry, Sturbridge, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 392 days.

(21) Appl. No.: 11/507,230

(22) Filed: Aug. 21, 2006

(65) Prior Publication Data

US 2008/0045795 A1    Feb. 21, 2008

(51) Int. Cl.
*A61B 1/00* (2006.01)
(52) U.S. Cl. .................. 600/152; 600/140; 600/143; 600/146
(58) Field of Classification Search .......... 600/114, 600/117, 118, 120–122, 139–152
See application file for complete search history.

(56) References Cited

U.S. PATENT DOCUMENTS

| | | | |
|---|---|---|---|
| 5,482,029 A | 1/1996 | Sekiguchi et al. | |
| 6,187,026 B1 * | 2/2001 | Devlin et al. | 606/205 |
| 6,293,907 B1 * | 9/2001 | Axon et al. | 600/114 |
| 6,562,021 B1 * | 5/2003 | Derbin et al. | 604/523 |
| 6,679,836 B2 | 1/2004 | Couvillon, Jr. | 600/146 |
| 6,770,027 B2 | 8/2004 | Banik et al. | 600/146 |
| 6,835,173 B2 | 12/2004 | Couvillon, Jr. | 600/146 |
| 6,887,235 B2 | 5/2005 | O'Connor et al. | 606/27 |
| 6,942,613 B2 | 9/2005 | Ewers et al. | 600/114 |
| 6,997,870 B2 * | 2/2006 | Couvillon, Jr. | 600/146 |
| 7,097,615 B2 * | 8/2006 | Banik et al. | 600/146 |
| 2003/0065373 A1 | 4/2003 | Lovett et al. | 607/122 |
| 2004/0176664 A1 | 9/2004 | Iddan | |
| 2005/0085693 A1 * | 4/2005 | Belson et al. | 600/146 |
| 2005/0203382 A1 | 9/2005 | Govari et al. | 600/424 |
| 2005/0250990 A1 | 11/2005 | Le et al. | |
| 2005/0272976 A1 | 12/2005 | Tanaka et al. | |
| 2006/0060207 A1 | 3/2006 | Hedge et al. | 128/848 |
| 2006/0111618 A1 * | 5/2006 | Couvillon, Jr. | 600/152 |
| 2006/0258912 A1 * | 11/2006 | Belson et al. | 600/152 |

FOREIGN PATENT DOCUMENTS

| EP | 1787575 A1 | 5/2007 |
|---|---|---|
| WO | 2006028019 A1 | 3/2006 |

OTHER PUBLICATIONS

Extended European Search Report, EP07016246, Dec. 14, 2007, 9 pages.

* cited by examiner

*Primary Examiner*—John P Leubecker
*Assistant Examiner*—Samuel Candler
(74) *Attorney, Agent, or Firm*—St. Onge Steward Johnston & Reens LLC

(57) ABSTRACT

A flexible endoscope providing increased control to an operator or user, the flexible endoscope utilizing an ionic polymeric material positioned in the shaft of the endoscope, such that, upon application of an electrical current to the ionic polymeric material, the material contracts and becomes relatively rigid. The flexible endoscope may further include mechanical controls for control of the flexible shaft allowing the user to simultaneously actuate both the polymeric material and mechanically deflect the shaft.

16 Claims, 4 Drawing Sheets

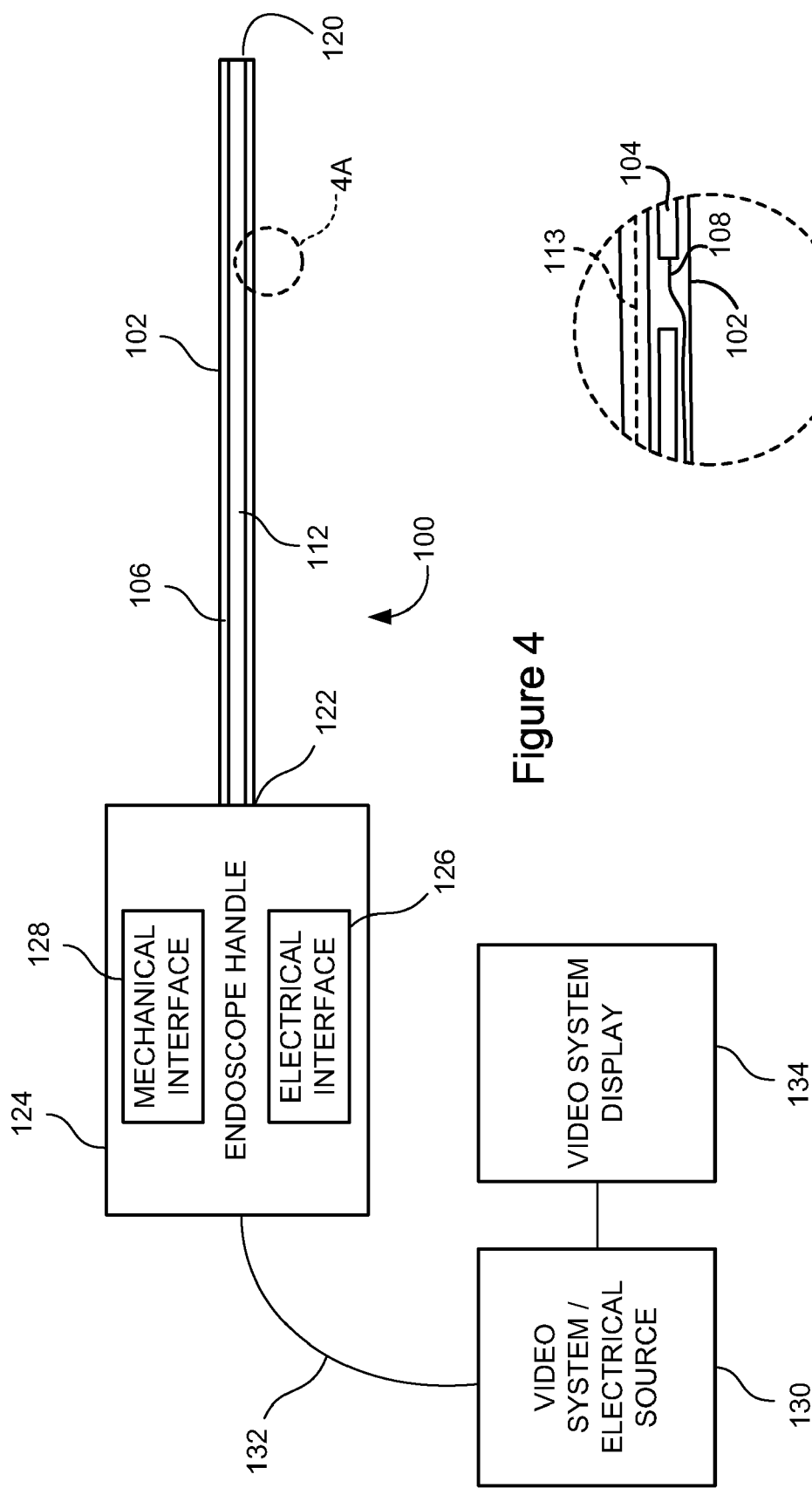

VARIABLE SHAFT FLEXIBILITY IN ENDOSCOPE

FIELD OF THE INVENTION

The invention relates to an endoscope having a flexible shaft member, and more specifically to an endoscope that has a shaft of varying flexibility upon the application of an electrical current to an ionic polymer material positioned in the shaft.

BACKGROUND OF THE INVENTION

Endoscopes provide a number of advantages when used in minimally invasive surgical procedures allowing the physician to view the surgical area, whether by direct visualization (e.g. via an eyepiece) or via a video screen that displays image data picked-up by a video endoscope. In any event, it is critical that the physician be provided with a clear and unobstructed view of the area ahead of the endoscope.

One challenge faced with the use of endoscopes is positioning the endoscope into a tight or difficult to access areas within a body cavity. For example, it may be necessary to view an area inside an internal organ, which requires the endoscope to be repeatedly bent or deflected. It is understood that it is highly undesirable to impinge upon the internal organ with the endoscope so as not to damage the surrounding tissue. This can become especially challenging when the endoscope must be deflected at a severe angle.

Accordingly, flexible endoscopes have been in use for some time. However, the flexibility and control of known endoscopes is limited. For example, it may be desirable, depending upon the application and use, to bend only a portion of the endoscope shaft at a severe angle while maintaining the endoscope shaft relatively straight both ahead or behind the bent portion of the shaft. Alternatively, it may be necessary to severely bend the shaft in several opposing directions while maintaining a relatively straight shaft between the bent portions. Current systems to not allow adequate shaft flexibility and control for difficult to access areas to be viewed, while at the same time, providing a cost effective and relatively simple design.

A number of systems have, with limited success, sought to provide a flexible endoscope shaft having increased control. For example, U.S. Pat. No. 6,942,613 ("Ewers et al.") discloses a method for placing an advancing a diagnostic or therapeutic instrument in a hollow body organ of a tortuous or unsupported anatomy. Ewers et al. teaches use of an "overtube" into which a colonoscope may be inserted. Ewers et al. uses electrical wires, which are positioned in tunnels that extend the length of the overtube. Upon application of an electrical current, the diameter of the tunnels contracts such that the wires come into contact with the inside of the tunnel surface causing the overtube to become rigid because the wire is not allowed to slip longitudinally with respect to the tunnel. While this provides some increased control, this device is separate from the scope that is used, which increases the size and the diameter of the device to be inserted into the cavity. For precise endoscopic procedures, this is unacceptable. Further, Ewers et al. does not allow for a contraction or expansion of the length of the endoscope shaft and, in fact, states that this feature is undesirable. (See, Col. 3, lines 21-24; Col. 4, lines 4-8.) In addition, Ewers et al. does not provide for specific control of one or more area of the shaft where the length of the shaft in a particular area may be altered or made more rigid.

U.S. Pat. No. 6,770,027 (Banik et al.) describes an endoscope apparatus that uses one or more electronically controlled actuators (e.g. electroactive polymer actuators) controlling the operation of the endoscope portion based on received control signals. However, Banik et al. is disadvantageously provided as a disposable or a single use device. (See e.g., Col. 2, lines 7-9 & 64-67; Col. 3, lines 4, 6, 9 & 13; Col. 4, lines 23-28; Col. 6, lines 41 & 50-51.) This disadvantageously means that the endoscope can not also be utilized as a standard mechanically flexible endoscope. In addition, Banik et al. due to among other things "single use economics", uses "wireless interface chipsets" rather than "electrical connections." However, power signals cannot be sent in a wireless format, and therefore, Banik et al. has resorted to providing a portable power source for providing power to the actuators. While having a relatively short-term use battery for a disposable system is feasible, providing a battery to power a non-disposable endoscope is highly undesirable as such a power source would dramatically increase the size and the weight of the device.

Accordingly, what is desired then is a flexible endoscope that may be used both as a mechanically deflectable endoscope and further uses a material that may change characteristics upon the application of a stimulus, such as, for example, and electrical current.

It is further desired to provide a flexible endoscope that is re-usable that employs a material that may change characteristics upon the application of a stimulus and that is relatively light-weight.

It is still further desired to provide a flexible endoscope that may be used both as a mechanically deflectable endoscope and uses a material that may change characteristics upon the application of a stimulus such that, the physician is provided specific control of one or more area of the shaft whether manually or by means of the change in material characteristics.

It is yet further desired to provide a flexible endoscope that is re-usable that employs a material that may change characteristics upon the application of a stimulus where the length of the shaft in a particular area of the endoscope may be altered or made more rigid.

SUMMARY OF THE INVENTION

These and other objects are achieved in one advantageous embodiment by the provision of an endoscope device that provides both mechanical control of and employs a material along the length of the endoscope shaft that may change characteristics upon the application of a stimulus.

In one embodiment, the endoscope uses a fibrous ionic polymeric material or similar material which changes in physical characteristics (such as length and rigidity) in response to an applied electrical current to achieve variable shaft rigidity, which is controllable by the operator. The endoscope is further provided as a conventional endoscope that may be deflected by mechanical means, providing the operator with total control of the endoscope.

The polymeric material may be provided as layers of chemically activated polymers, such as fibrous ionic polymer. The layers may be placed in one or more section or layers and attached in one or more points and may be combined with additional mechanical components. Under control of the operator, the rigidity of the endoscope shaft can be changed to enable the operator to navigate and/or pass through difficult sections while still maintaining maximum flexibility for examination purposes.

The relatively thin layers of polymeric material may further be applied as, for example, a tube integral with and around the shaft of the endoscope in one or more sections. It is contemplated that the layer(s) of polymeric material may be constrained at one or more points to the shaft. In this manner, the application of a stimulus, such as, for example, an electrical current, will cause the polymeric material to contract over the flexible shaft section. Depending on the fixture, this will act to temporarily "stiffen" the section and reduce its "flexibility." When this current is removed, however, the material relaxes restoring the original flexibility to the endoscope so that the operator can use the flexible endoscope in a conventional fashion.

It is still further contemplated that multiple sections containing the polymeric material may be used, and may also be fixed in opposition to each other along the length of the endoscope shaft to provide still further control of the endoscope for the operator. The shaft configuration as described herein may, for example, be used with a wide variety of endoscopes including, video endoscopes or those that use and eyepiece for visualization.

In one advantageous embodiment a flexible endoscope is provided comprising a flexible shaft portion having a distal and a proximal end. The flexible shaft portion includes a flexible outer layer and at least one elongated segment disposed in the flexible outer layer and comprising a polymer material that changes characteristics upon the application of an electrical current. The flexible endoscope further comprises a handle portion coupled to the flexible shaft portion, an electrical source for providing the electrical current to the at least one elongated segment, and at least one electrical conductor electrically connected between the at least one elongated segment and the electrical source. The endoscope is provided such that the electrical conductor extends from the flexible shaft portion through the handle portion to the electrical source.

In another advantageous embodiment a flexible endoscope is provided comprising a flexible shaft portion having a distal and a proximal end. The flexible shaft portion includes a flexible outer layer, an inner layer enclosed by the flexible outer layer, and at least one elongated segment disposed in the flexible outer layer and comprising a polymer material that changes characteristics upon the application of an electrical current, the at least one segment having first and second ends. The flexible endoscope further includes an electrical source for providing the electrical current to the at least one elongated segment. The flexible endoscope is provided such that the at least one elongated segment has at least one end affixed to the inner layer and further includes a handle portion coupled to the flexible shaft portion.

In still another advantageous embodiment a method for operating a flexible endoscope is provided comprising the steps of enclosing a flexible endoscope shaft in an inner layer, enclosing the inner layer with a flexible outer layer, and depositing at least one elongated segment in the outer layer. The method further comprises the steps of electrically connecting an electrical conductor between the at least one elongated segment and an electrical source, selectively actuating controls to apply an electrical current to the at least one elongated segment, and deflecting the flexible endoscope shaft according to the applied electrical current.

Other objects of the invention and its particular features and advantages will become more apparent from consideration of the following drawings and accompanying detailed description.

BRIEF DESCRIPTION OF THE DRAWINGS

FIG. 4 is a block diagram of the advantageous embodiment according to FIG. 1.

FIG. 4A is a detail view of a portion of FIG. 4.

DETAILED DESCRIPTION OF THE INVENTION

Figure 1:
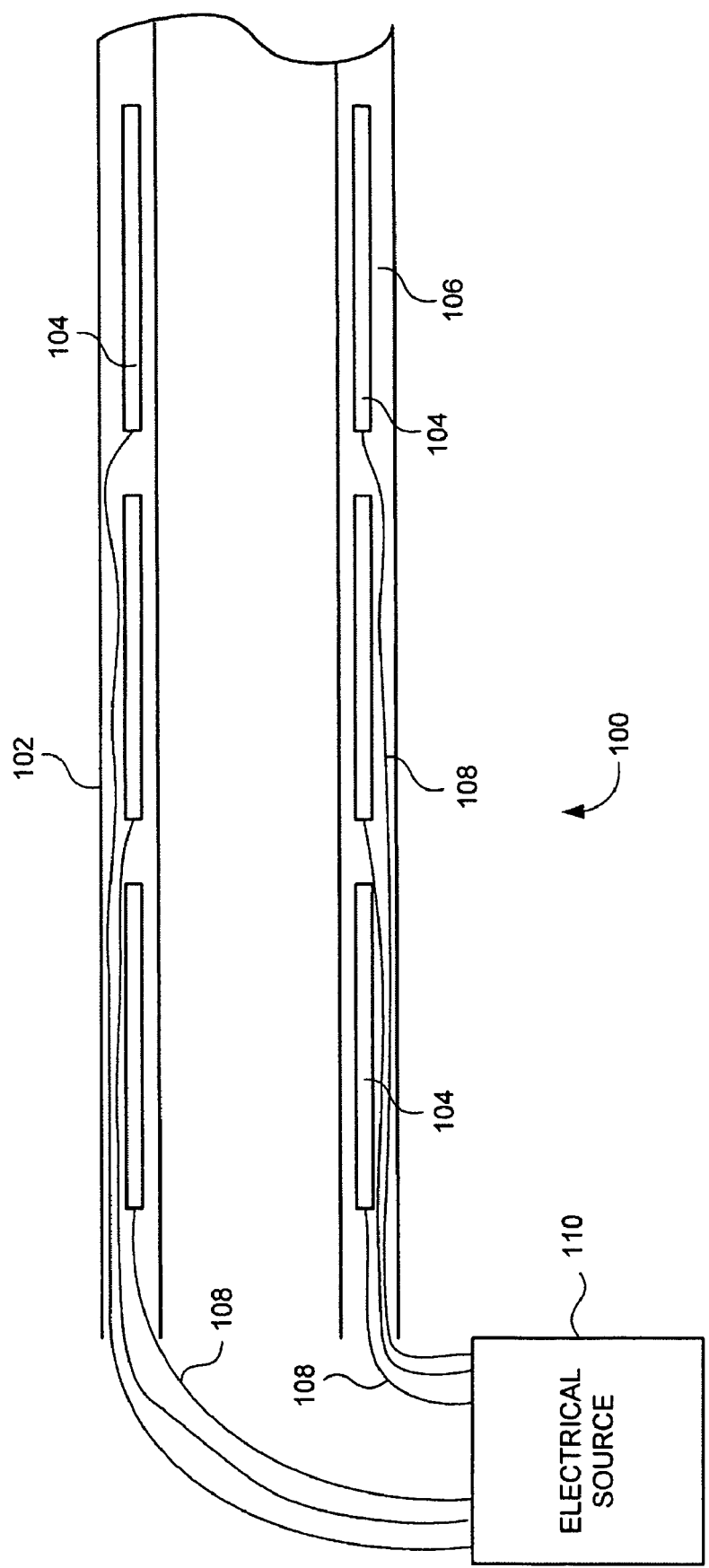
FIG. 1 is an illustration of one advantageous embodiment depicting a portion of the flexible endoscope shaft in which a plurality of segments is positioned along the endoscope shaft.

Referring now to the drawings, wherein like reference numerals designate corresponding structure throughout the views.

FIG. 1 is an illustration of a portion of a shaft 102 of flexible endoscope 100. The shaft 102 is shown as a sectional view including elongated segments 104, which are positioned within an outer layer 106 of the shaft 102.

Also illustrated in FIG. 1 are electrical conductors 108, which are individually electrically connected to the various elongated segments 104. The electrical conductors 108 generally extend from their respective elongated segment 104, through the outer layer 106 and are electrically coupled to an electrical source 110.

The elongated segments 104 are provided as, for example, a fibrous ionic polymeric material (or similar material), which changes in physical characteristics (such as length and rigidity) in response to a stimulus. In this case, the stimulus is an applied electrical current. In this manner, the applied electrical current may be used to achieve variable shaft rigidity, which is controllable by the operator or user. For example, as an electrical current is applied to a particular elongated segment 104, the elongated segment 104 has a tendency to contract and/or become more rigid. In this manner, the shaft 102 may be deflected toward the side on which the simulated elongated segment 104 is located. Multiple segments may further be actuated to provide for severe deflection of the shaft 102. This is highly desirable for the insertion of the endoscope into body cavities having tortuous bends or turns.

In addition to the shaft deflection by means of the of the elongated segments 104, the endoscope 100 may further be manipulated by conventional mechanical means, such as, for example, standard cables/wires extending along the length of the shaft 102, which engage with various portions of the flexible endoscope. In this manner, the endoscope 100 may be inserted into a body cavity having a severe or tortured pathway, but still allow the operator or user full control of the endoscope 100 once the location for the procedure is reached. It is contemplated that the endoscope 100 will be able to maintain the deflected shape during the procedure so as not to put pressure on the surrounding tissue or even displace or damage the tissue.

It is still further contemplated that the both the electrical and the mechanical means may be simultaneously used providing absolute control for the operator or user.

Electrical source 110 may be provided as a current source and while each electrical conductor 108 is illustrated connected to the electrical source 110, it is contemplated that controls are provided to selectively provide electrical current to each elongated segment 104. In addition, the amount of deflection and rigidity of each elongated segment 104 may be individually controlled based on the total amount of electrical current that is supplied to each elongated segment 104. For example, greater deflection of a particular elongated segment 104 may be achieved by the application of an increased current. In this manner, a relatively large amount of variable control is provided to the operator or user.

It is further contemplated that the outer layer 106 may, in one advantageous embodiment, comprise an electrically insulated water-tight material to seal the shaft 102.

Figure 2:
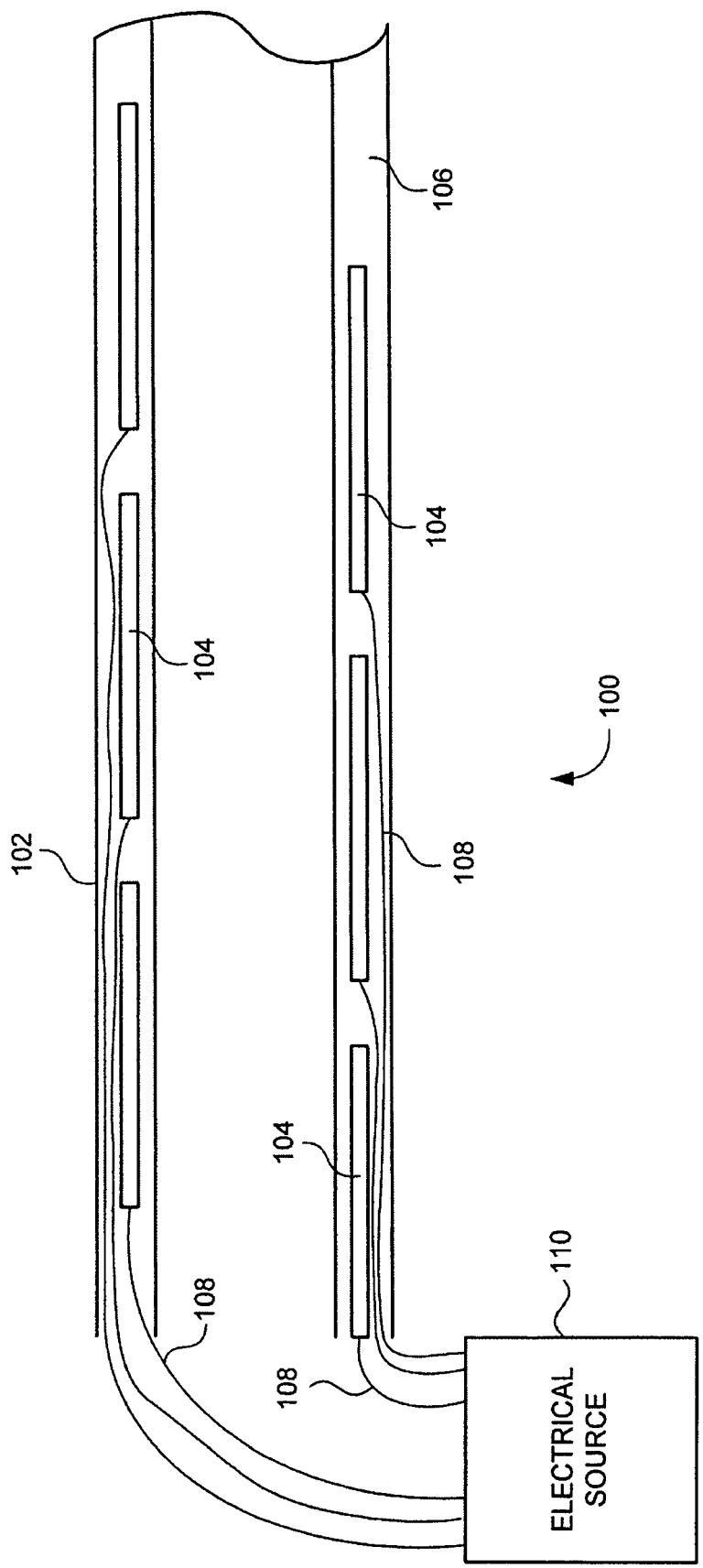
FIG. 2 is an illustration of an alternative configuration of the plurality of segments according to FIG. 1.

The elongated segments are positioned in an end-to-end fashion and may be radially positioned about shaft 102 as illustrated in FIG. 1. However many differing configurations are contemplated. For example, FIG. 2 illustrates an alternative embodiment for the placement of the elongated segments 104.

In this configuration, the elongated segments 104 are staggered with respect to each other along the length of the shaft 102. In this manner, increased control is provided to the operator or user. Many differing configurations of the placement of the elongated segments 104 are possible, whether altering the longitudinal placement or the radial placement of the segments as desired to achieve particular control and deflection of the shaft 102.

Figure 3:
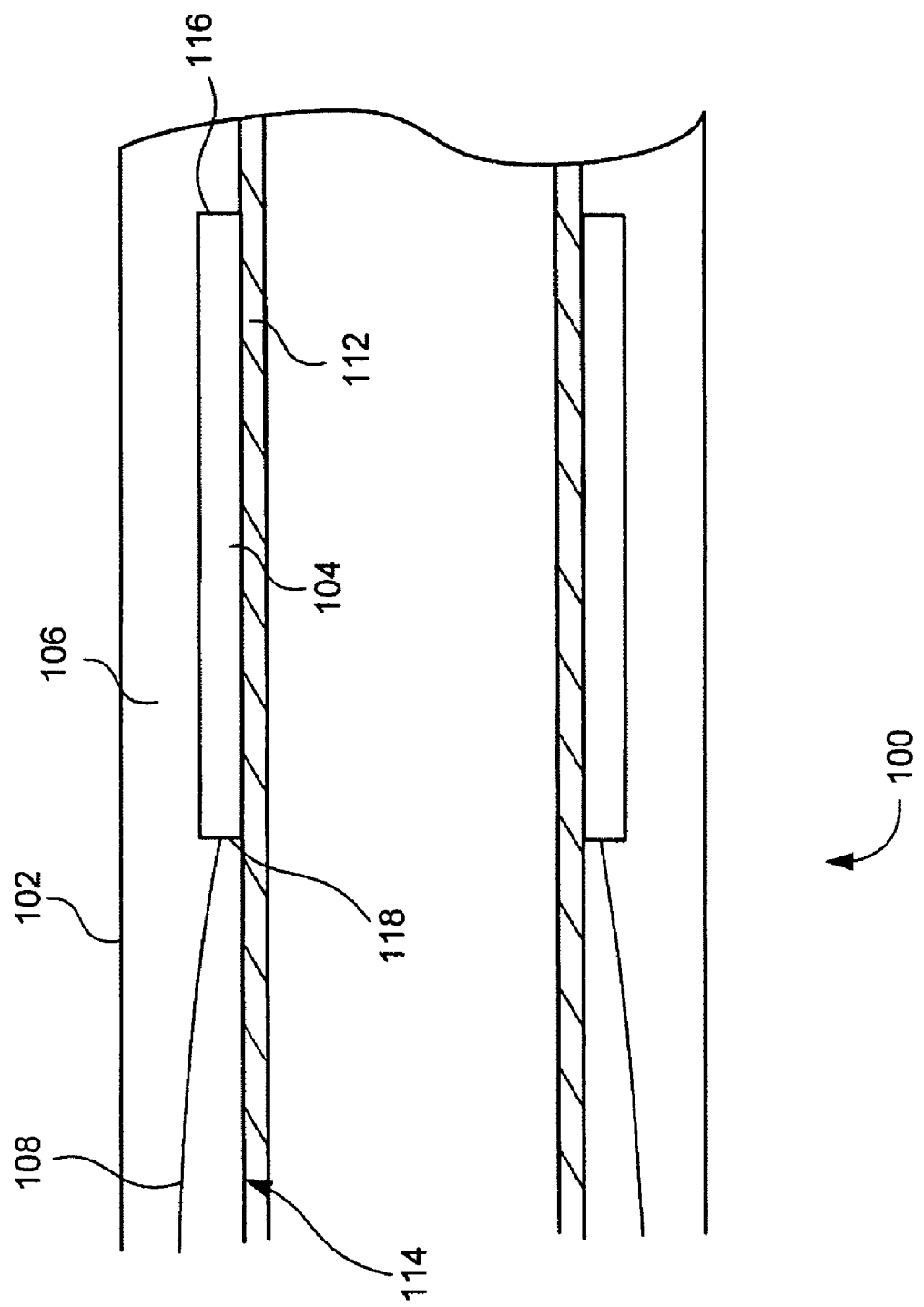
FIG. 3 is an enlarged view of the embodiment depicted in FIG. 1 showing an inner surface of the shaft.

Referring now to FIG. 3, a section of the shaft 102 is illustrated. The shaft 102 includes outer layer 106, in which, elongated segment 104 is positioned. Also illustrated is inner layer 112, which is positioned along an inner surface 114 of outer layer 106.

It is contemplated that inner layer 112 may, in one advantageous embodiment, comprise a braided material, such as for example, a braided metal material. Alternatively, the inner layer 112 may comprise, for example, a slotted tube or other flexible material or a combination of both braided and flexible material.

In another advantageous embodiment, the elongated segment 104 is affixed at end 116 to inner layer 112. Alternatively, it is contemplated that both end 116 and end 118, may be affixed or attached to inner layer 112. Accordingly, the elongated segment 104 is compressed between the outer layer 106 and the inner layer 112.

In operation, upon the application of an electrical current to elongated segment 102 via electrical conductor 108, elongated segment 102 will contract causing the shaft to become harder and less flexible. The contraction of the elongated segment 104 causes the inner layer 112, whether comprising a braided material, a slotted tube, other flexible material, or combinations thereof, to displace with respect to the outer layer 106 providing the operator or user with increased control of the shaft 102.

It should further be noted that, while the embodiments depicted illustrated used of elongated segments 102 of ionic polymer or similar material, it is contemplated that the entire shaft 102 may comprise the ionic polymer provided as a continuous layer. The continuous layer is supplied electrical current via electrical conductor 108 as previous described herein. In addition, the continuous layer may also be provided with the inner layer 112 as discussed above.

Turning now to FIG. 4, a block diagram of endoscope 100 is illustrated. The shaft 102 is illustrated including both the outer layer 106 and the inner layer 112. The endoscope 100 is illustrated as comprising a video endoscope, however, it is contemplated that the endoscope 100 may be configured with an eyepiece for direct viewing by the operator or user.

When used as a video endoscope, endoscope 100 may be provided with an imager (not shown) positioned at a distal end 120 of shaft 102. The imager may be provided, for example, as a Charged Coupled Device (CCD) or a CMOS device as desired, and may be provided as a hard-wired or wireless device.

The shaft 102 is coupled at a proximal end 122 to handle 124 of endoscope 100. The handle 124 is provided having both an electrical interface 126 and a mechanical interface 128 provided for the operator or user. The electrical interface 126 may be provided as a series of buttons to actuating select elongated segments 104. The mechanical interface may comprise any standard interface for mechanically actuating the flexible shaft 102. For example, the mechanical interface may comprise a series of levers, knobs, buttons, etc., which interact with a series of wires or cables 113 (FIG. 4A) to mechanically deflect shaft 102 as desired. However, it is contemplated that the electrical interface will, in addition to the mechanical control, allow the operator or user to make portions of the shaft 102 rigid and/or deflect the shaft 102 at relatively severe angles. The combination of both electrical control of the polymeric material and mechanical control of the flexible endoscope shaft 102 provides increased control, which is highly desirable when performing a procedure in a hard-to-access body cavity.

Also illustrated in FIG. 4 is video system 130, which may further comprise electrical source 110. Video system 130 is provided to receive and process image data generated by the imager (not shown) in a video endoscope configuration. In addition, a conductor 132 is provided to supply electrical current to the handle 124, which is selectively applied to the polymeric material according to the electrical interface actuated by the operator or user. It is further contemplated that the conductor 132, may comprise an optical cable for supplying illuminating light to the endoscope 100 and may comprise a data channel for receiving image data generated by the imager.

Alternatively, a light source, such as an LED, may be positioned in the endoscope, whether in handle 124 or shaft 102, which receives power from electrical source 110 and generated illuminating light. In this embodiment, the conductor 132 need not comprise a light channel. Still further, as previously mentioned, the imager may be provided as a wireless transmitter, in which case, conductor 132 need not contain a data channel.

While electrical source 110 has been illustrated as external to handle 124, it is contemplated that in one embodiment, it may be positioned in handle 124 as desired or a portion thereof may be positioned in handle 124. For example, a power connection may be provided to handle 124, while the power conditioning may be performed in handle 124. Alternatively, conditioned power may simply be provided to handle 124.

Also illustrated in FIG. 4 is video system display 134, which may comprise virtually any type of video screen desired by the operator or user, such as, for example, a CRT, an LCD or similar screen. In this manner, the operator or user may clearly view the area ahead of the distal end 120 of shaft 102 to perform the procedure.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A flexible endoscope comprising:
  a flexible shaft portion having a distal and a proximal end and including:
    an outer layer comprising an electrically insulated water-tight material;
    an inner layer enclosed by said outer layer;

a plurality of elongated segments disposed in said outer layer and comprising a polymer material that changes characteristics upon the application of an electrical current;

a handle portion coupled to said flexible shaft portion;

an electrical source for providing the electrical current to said at least one elongated segment; and electrical conductors electrically connected between said plurality of elongated segments and said electrical source;

said electrical conductors extending from said flexible shaft portion through said handle portion to said electrical source;

wherein said plurality of elongated segments are positioned in said outer layer in an end-to-end fashion along a longitudinal length of said flexible shaft portion and each elongated segment has at least one end affixed to said inner layer such that upon an application of electrical current to said plurality of elongated segments, said plurality of elongated segments change physical dimension; and wherein said inner layer moves relative to said outer layer based on the dimensional change of at least one of said plurality of elongated segments.

2. The flexible endoscope according to claim 1 wherein said inner layer is selected from the group consisting of: a braided material, a slotted tube and combinations thereof.

3. The flexible endoscope according to claim 1 wherein said elongated segments are further radially positioned around said flexible shaft portion substantially opposite each other.

4. The flexible endoscope according to claim 1 wherein said elongated segments are further radially positioned around said flexible shaft portion in a substantially staggered arrangement relative to each other.

5. The flexible endoscope according to claim 1 wherein said at least one elongated segment comprises a continuous ionic polymer material extending along a length of said flexible shaft portion.

6. The flexible endoscope according to claim 1 wherein said handle portion comprises an interface for issuing commands to said at least one elongated segment for control of said flexible shaft portion.

7. The flexible endoscope according to claim 1 wherein said endoscope comprises a video endoscope and further comprises a video system for processing video data generated by said endoscope.

8. The flexible endoscope according to claim 7 further comprising a display for displaying the video data to a user.

9. The flexible endoscope according to claim 1 wherein said endoscope further comprises a mechanically actuatable endoscope comprising cables in said flexible shaft portion such that a user may deflect said flexible shaft portion either by application of electrical current to said at least one elongated segment, or by mechanical actuation of said cables in the flexible shaft portion, or both.

10. A flexible endoscope comprising:

a flexible shaft portion having a distal and a proximal end and including:

an outer layer comprising an electrically insulated water-tight material;

an inner layer enclosed by said outer layer;

at least two elongated segments disposed in said outer layer and comprising a polymer material that changes characteristics upon the application of an electrical current, said at least one segment having first and second ends;

an electrical source for providing the electrical current to said at least two elongated segments;

said at least two elongated segments each having at least one end affixed to said inner layer;

a handle portion coupled to said flexible shaft portion;

wherein upon an application of electrical current to said at least two elongated segments, said at least two elongated segments change physical dimension; and wherein said inner layer moves relative to said outer layer based on a dimensional change of at least one of said at least two elongated segments.

11. The flexible endoscope according to claim 10 wherein said inner layer is selected from the group consisting of: a braided material, a slotted tube and combinations thereof.

12. The flexible endoscope according to claim 10 wherein said at least one elongated segment comprises a plurality of elongated segments positioned in said flexible outer layer.

13. The flexible endoscope according to claim 10 wherein said endoscope further comprises a mechanically actuatable endoscope comprising cables in said flexible shaft portion, such that, a user may deflect said flexible shaft portion either by application of electrical current to said at least one elongated segment, or by mechanical actuation of said cables in the flexible shaft portion, or both.

14. A method for operating a flexible endoscope comprising the steps of:

providing an inner layer;

enclosing the inner layer with an outer layer, the outer layer comprising an electrically insulated water-tight material;

depositing at least two elongated segments in the outer layer;

electrically connecting electrical conductors between the at least two elongated segments and an electrical source;

affixing at least one end of each of the at least two elongated segments to the inner layer;

selectively actuating controls to apply an electrical current to the at least two elongated segments;

deflecting the flexible endoscope shaft according to the applied electrical current; and wherein the inner layer moves relative to the outer layer based on a dimensional change of at least one of the at least two elongated segments.

15. The method according to claim 14 wherein the electrical conductor extends from the at least one elongated segment, through a handle portion to the electrical source.

16. The method according to claim 14 further comprising the steps of actuating a mechanical control that includes cables in the flexible endoscope shaft to mechanically deflect the flexible endoscope shaft with the cables.

* * * * *